(12) United States Patent
Bhagchandani et al.

(10) Patent No.: US 9,656,043 B2
(45) Date of Patent: May 23, 2017

(54) MULTI-SPLIT-TIPPED CATHETER

(75) Inventors: Neha S. Bhagchandani, Bloomington, IN (US); Ryan Nowicki, Indianapolis, IN (US); Michael R. Kurrus, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/334,838

(22) Filed: Dec. 22, 2011

(65) Prior Publication Data

US 2012/0232472 A1 Sep. 13, 2012

Related U.S. Application Data

(60) Provisional application No. 61/450,331, filed on Mar. 8, 2011.

(51) Int. Cl.
*A61M 1/00* (2006.01)
*A61M 25/00* (2006.01)
*A61M 1/36* (2006.01)

(52) U.S. Cl.
CPC ...... *A61M 25/0071* (2013.01); *A61M 1/3661* (2014.02); *A61M 25/0026* (2013.01); *A61M 25/007* (2013.01); *A61M 25/0032* (2013.01); *A61M 2025/0031* (2013.01); *A61M 2025/0079* (2013.01)

(58) Field of Classification Search
CPC .......... A61M 25/0026; A61M 25/0028; A61M 25/0029; A61M 25/003; A61M 25/0032; A61M 25/0067; A61M 25/0068; A61M 25/0069; A61M 25/0071; A61M 1/3661; A61M 2025/0031; A61M 2025/0079; A61M 25/007

USPC .............. 604/27, 35, 43, 264, 266, 523, 284
See application file for complete search history.

(56) References Cited

U.S. PATENT DOCUMENTS

| | | | |
|---|---|---|---|
| 4,902,276 A * | 2/1990 | Zakko | A61B 17/22 604/28 |
| 5,209,723 A | 5/1993 | Twardowski et al. | |
| 5,346,471 A | 9/1994 | Raulerson | |
| 5,348,536 A | 9/1994 | Young et al. | |
| 5,360,397 A | 11/1994 | Pinchuk | |
| 5,403,291 A | 4/1995 | Abrahamson | |
| 5,405,320 A | 4/1995 | Twardowski et al. | |
| 5,405,341 A * | 4/1995 | Martin | A61M 25/0026 604/284 |
| 5,451,206 A | 9/1995 | Young | |
| 5,480,380 A | 1/1996 | Martin | |
| 5,486,159 A | 1/1996 | Mahurkar | |
| 5,489,278 A | 2/1996 | Abrahamson | |
| 5,509,897 A | 4/1996 | Twardowski | |
| 5,556,390 A | 9/1996 | Hicks | |
| 5,569,182 A | 10/1996 | Twardowski et al. | |
| 5,776,096 A | 7/1998 | Fields | |

(Continued)

*Primary Examiner* — Andrew Gilbert
*Assistant Examiner* — Amber Stiles
(74) *Attorney, Agent, or Firm* — Woodard, Emhardt, Moriarty, McNett & Henry LLP

(57) ABSTRACT

A multilumen catheter with an inflow or an outflow lumen having at least two tube extensions extending from the distal end of the catheter that open into the inflow or outflow lumen. The catheter is useful in the extracorporeal treatment of blood, such as hemodialysis, hemofiltration or apheresis. A device to selectively test each of the two tube extensions for occlusion.

11 Claims, 5 Drawing Sheets

(56) References Cited

U.S. PATENT DOCUMENTS

| | | |
|---|---|---|
| 5,807,311 A | 9/1998 | Palestrant |
| 5,947,953 A | 9/1999 | Ash et al. |
| 5,961,485 A | 10/1999 | Martin |
| 5,961,486 A | 10/1999 | Twardowski et al. |
| 5,976,103 A | 11/1999 | Martin |
| 5,989,206 A | 11/1999 | Prosl et al. |
| 6,001,079 A | 12/1999 | Pourchez |
| 6,146,354 A | 11/2000 | Beil |
| 6,190,349 B1 | 2/2001 | Ash et al. |
| 6,206,849 B1 | 3/2001 | Martin et al. |
| 6,280,423 B1 | 8/2001 | Davey et al. |
| 6,293,927 B1 | 9/2001 | McGuckin |
| 6,409,700 B1 | 6/2002 | Siegel et al. |
| 6,461,321 B1 | 10/2002 | Quinn |
| 6,517,529 B1 | 2/2003 | Quinn |
| 6,540,714 B1 | 4/2003 | Quinn |
| 6,595,966 B2 | 7/2003 | Davey et al. |
| 6,638,242 B2 | 10/2003 | Wilson et al. |
| 6,695,832 B2 | 2/2004 | Schon et al. |
| 6,702,776 B2 | 3/2004 | Quinn |
| 6,719,749 B1 | 4/2004 | Schweikert et al. |
| 6,758,836 B2 | 7/2004 | Zawacki |
| 6,786,884 B1 | 9/2004 | DeCant et al. |
| 6,808,510 B1 | 10/2004 | DiFiore |
| 6,814,718 B2 | 11/2004 | McGuckin et al. |
| 6,858,019 B2 | 2/2005 | McGuckin et al. |
| 6,872,198 B1 | 3/2005 | Wilson et al. |
| 6,881,211 B2 | 4/2005 | Schweikert et al. |
| 6,916,313 B2 | 7/2005 | Cunningham |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,991,625 B1 | 1/2006 | Gately et al. |
| 6,997,894 B2 | 2/2006 | Caresio |
| 7,018,374 B2 | 3/2006 | Schon et al. |
| 7,066,925 B2 | 6/2006 | Gately et al. |
| 7,074,213 B2 | 7/2006 | McGuckin et al. |
| 7,077,829 B2 | 7/2006 | McGuckin et al. |
| 7,090,654 B2 | 8/2006 | Lotito et al. |
| 7,108,674 B2 | 9/2006 | Quinn |
| 7,141,035 B2 | 11/2006 | Haggstrom |
| RE39,451 E | 12/2006 | Kuhle |
| 7,182,746 B2 | 2/2007 | Haarala et al. |
| 7,211,074 B2 | 5/2007 | Sansoucy |
| 7,223,254 B2 | 5/2007 | Hjalmarsson |
| 7,229,429 B2 | 6/2007 | Martin et al. |
| D550,839 S | 9/2007 | Zawacki et al. |
| 7,276,043 B2 | 10/2007 | Heath |
| 7,282,041 B2 | 10/2007 | Igarashi et al. |
| 7,300,430 B2 | 11/2007 | Wilson et al. |
| 7,381,204 B2 | 6/2008 | Wilson et al. |
| 7,390,322 B2 | 6/2008 | McGuckin et al. |
| 7,393,339 B2 | 7/2008 | Zawacki et al. |
| 7,465,286 B2 | 12/2008 | Patterson et al. |
| 7,485,107 B2 | 2/2009 | DiFiore |
| 7,566,316 B2 | 7/2009 | McGuckin et al. |
| 7,569,029 B2 | 8/2009 | Clark |
| 7,575,563 B2 | 8/2009 | Appling |
| RE40,913 E | 9/2009 | Schweikert et al. |
| D603,044 S | 10/2009 | Appling et al. |
| 7,615,034 B2 | 11/2009 | DiFiore |
| 7,695,450 B1 | 4/2010 | Twardowski et al. |
| 2008/0009803 A1* | 1/2008 | Schon ............... A61M 25/0009 604/173 |
| 2008/0039774 A1* | 2/2008 | Zawacki ........... A61M 25/0026 604/43 |
| 2011/0071500 A1* | 3/2011 | Lareau ................. A61M 1/285 604/523 |

* cited by examiner

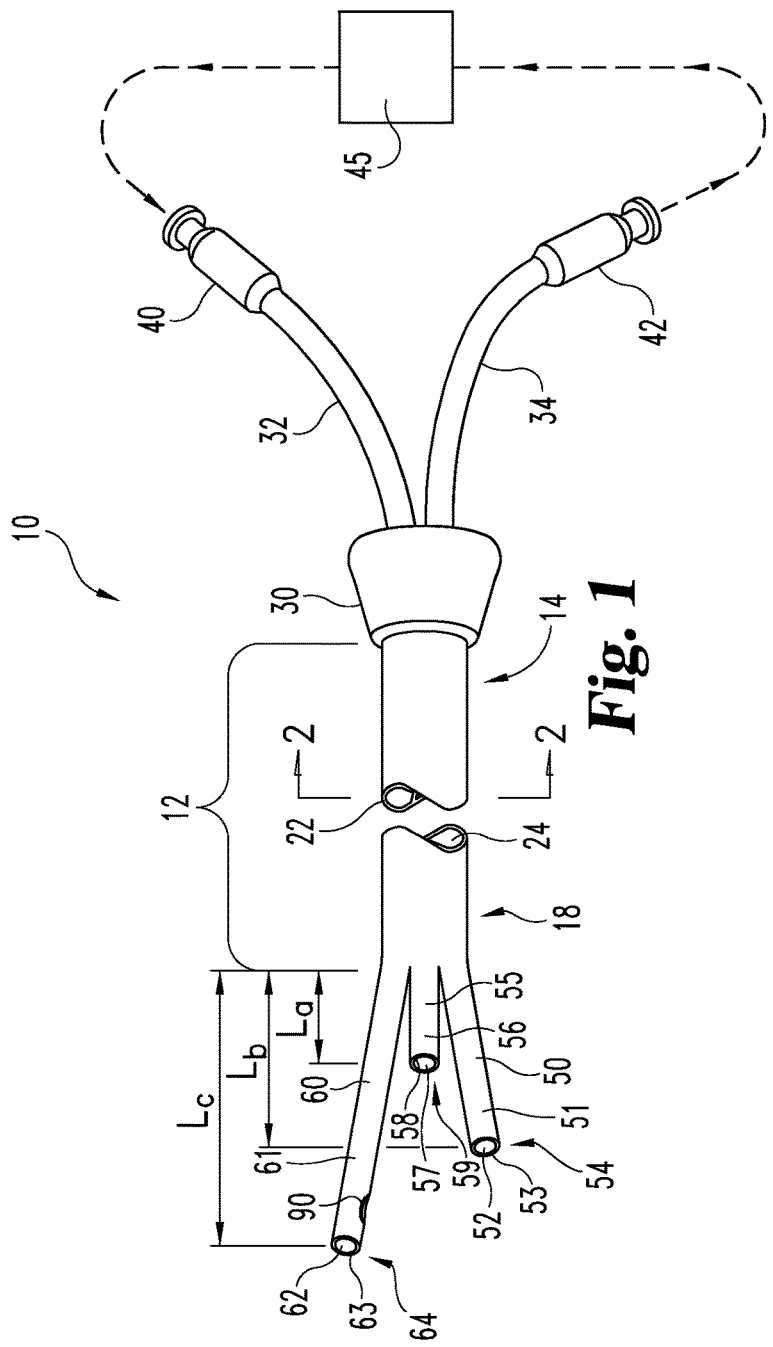
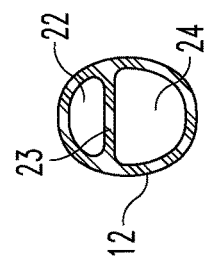

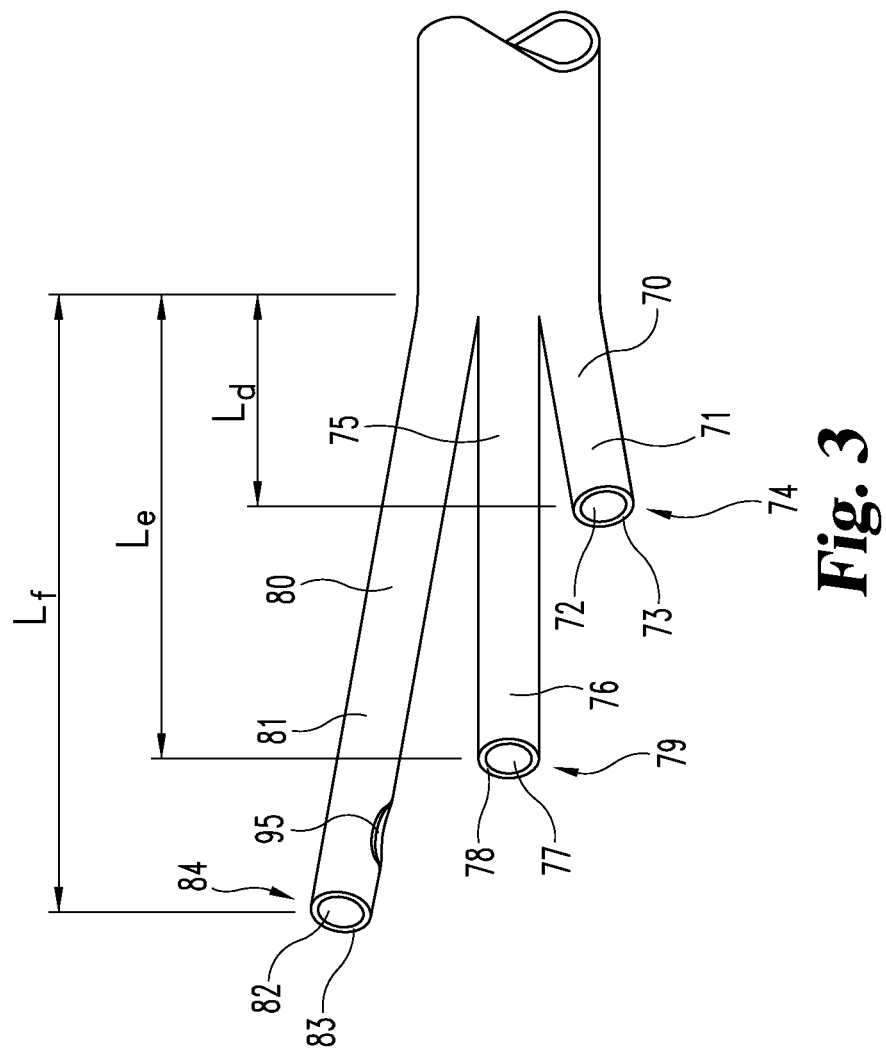

MULTI-SPLIT-TIPPED CATHETER

REFERENCE TO RELATED APPLICATION

This application claims the benefit of U.S. Provisional Patent Application No. 61/450,331, filed Mar. 8, 2011, which is hereby incorporated by reference in its entirety.

This disclosure relates generally to multilumen catheters used in the extracorporeal treatment of bodily fluids, and in particular aspects, relates to multilumen central venous catheters used for example in the extracorporeal treatment of blood, such as hemodialysis, hemofiltration or apheresis.

BACKGROUND

A catheter with two lumens is commonly used in a number of medical situations, such as in treatments of bodily fluids outside the patient. A common example occurs during hemodialysis. A dual lumen catheter is inserted into a large vein, usually the vena cava (by way of the internal jugular vein or the femoral vein) to allow large flows of blood to be withdrawn though one lumen, the aspiration lumen. The blood is then pumped from the aspiration lumen and through the hemodialysis machine where waste products such as creatine and urea are removed. Thereafter the dialyzed or clean blood is fed from the machine into the catheter's second lumen, the infusion lumen, where the blood returns to the vena cava or other vessel.

The lumens in such catheters can occasionally become obstructed, which reduces the flow rate of bodily fluids. The distal tip of the aspiration lumen, for example, may be inadvertently placed against the walls of the vein, which restricts or altogether blocks the flow into the aspiration lumen. Or after a period of time, a fibrin sheath may grow around the distal tip of the catheter. A fibrin sheath is a build-up of cells that encases the catheter and when present, impairs blood flow in and out of the catheter.

Achieving adequate flow is the Achilles heel to extracorporeal treatment of bodily fluids. Hence, it is preferred that the access lines to the body, e.g. catheter lumen(s), remain unobstructed. To this end, some dual lumen catheter designs include holes in the side of the catheter, near the distal end, that open into the aspiration and infusion lumens to increase access and flow. Others split the distal portion of the catheter into two tubes of unequal length, separating the aspiration lumen from the infusion lumen to avoid obstruction. While these designs may combat obstructions, lumen blockage and reduced flows continue to be a problem. The following disclosure further addresses that need.

SUMMARY

This Summary is provided merely to introduce certain concepts and not to identify any key or essential features of the claimed subject matter.

In one aspect, the present disclosure provides an improved split-tip multilumen catheter that avoids being obstructed during the extracorporeal treatment of bodily fluids. The device includes at least two tubes extending from a catheter's tip that open into a single lumen to increase the flow in or out of the lumen.

In another aspect, the present disclosure provides a multilumen catheter that avoids being obstructed during hemodialysis, hemofiltration or apheresis. The device includes at least two tubes near the catheter's distal tip that open into the same aspiration lumen to increase the flow into and through the aspiration lumen.

In yet another aspect, the present disclosure provides a device to test for an obstruction in multiple catheter tips that open to a common lumen. The device includes a multilumen catheter that is placed in the common lumen and selectively provides vacuum access to each tip.

BRIEF DESCRIPTION OF THE DRAWINGS

FIG. 1 depicts a plan view according to one embodiment of the present disclosure.

FIG. 2 depicts a cross-sectional view of one embodiment of the present disclosure.

FIG. 3 depicts a plan view of another embodiment of the present disclosure.

DETAILED DESCRIPTION OF THE ILLUSTRATED EMBODIMENTS

Figure 4:
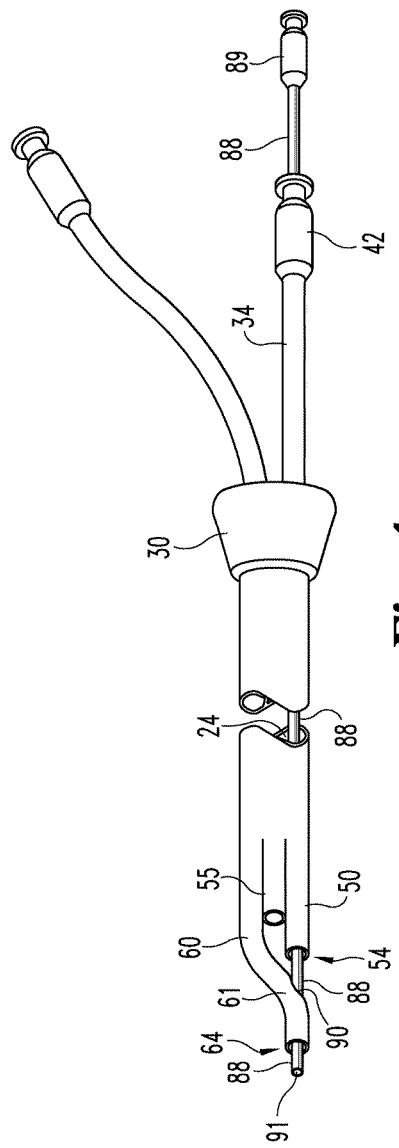
FIG. 4 depicts a plan view of one embodiment of the present disclosure preloaded onto an obturator.

For the purposes of promoting an understanding of the principles of the disclosure, reference will now be made to certain embodiments depicted in the drawings and specific language will be used to describe them. The reader should understand that no limitation of the scope of the claims is intended by using specific language. Alterations, modifications, and further applications of the principles of the disclosure are also included in the scope of this disclosure as they would normally occur to one of ordinary skill in this technology.

Among other things, the present disclosure provides a multilumen catheter to treat bodily fluids outside the body. The bodily fluids are pumped from the body through an aspiration lumen, treated, and then returned to the body through an infusion lumen. By way of example, the disclosed embodiments are described for use in hemodialysis. Additional non-limiting examples would also include apheresis and hemofiltration, as those of ordinary skill in this art will readily understand, as well as other uses in the extracorporeal treatment of bodily fluids or for other medical indications or situations.

FIG. 1 depicts a multilumen catheter 10 in one embodiment. Catheter 10 is not shown to scale to avoid obscuring finer details, it being contemplated that various lengths and component sizes would be adjusted as needed for the particular patient and procedure involved. Catheter 10 includes an elongated flexible tubular member 12 having a proximal end portion 14 and a distal end portion 18. Catheter 10 is shown in FIGS. 1 and 2 with two lumens extending through it; one is infusion lumen 22 and the other is aspiration lumen 24. Elongated flexible tubular member 12 has a generally oval exterior cross-section and lumens 22 and 24 have generally D-shaped internal open profiles. Additional catheter cross-sections and lumen profiles are, however, usable with this disclosure, such as round, oval, egg-shaped, or rectangular. Lumens 22 and 24 are separated by septum 23 and as shown, aspiration lumen 24 preferably has a larger open profile than infusion lumen 22.

The illustrated embodiment of catheter 10 includes a conventional bifurcated fitting at its proximal end, such as hub 30. Hub 30 may be provided with conventional suture wings (not shown) if desired to attach the catheter to the patient's skin. Flexible extension tubes 32, 34 extend in the proximal direction from hub 30. Flexible extension tube 32 is in fluid communication with infusion lumen 22 and flexible extension tube 34 is in fluid communication with aspiration lumen 24. Flexible extension tubes 32, 34 may also be provided with conventional clamps (not shown) to selectively stop flow through either extension tube. Luer locks or other suitable connecting mechanisms 40, 42 are placed at the proximal ends of tubes 32, 34 to attach catheter 10 to a treatment instrument 45 (such as a dialyzer). Luer lock 42 provides fluid engagement between aspiration lumen 24 and the input to instrument 45 and Luer lock 40 provides fluid engagement between infusion lumen 22 and the output from instrument 45.

Catheter 10 further includes at least three distal end tubes attached to the distal end portion 18 of elongated flexible tubular member 12. The first distal end tube 50 has an outer surface 51 and defines a first passageway 52 extending longitudinally through distal end tube 50, terminating at aspiration port 54 at distal end 53. The second distal end tube 55 has an outer surface 56 and defines a second passageway 57 extending longitudinally through distal end tube 55, terminating at aspiration port 59 at distal end 58. The third distal end tube 60 has an outer surface 61 and defines a third passageway 62 extending longitudinally through distal end tube 60, terminating at infusion port 64 at distal end 63. The first and second passageways 52, 57 are in fluid communication with aspiration lumen 24, which extends the full length of catheter 10. Third passageway 62 is in fluid communication with infusion lumen 22, which also extends the full length of catheter 10.

The first, second, and third distal end tubes 50, 55, 60 preferably have outer surfaces that are contiguous and/or continuous with the outer surface of elongated flexible tubular member 12 and extend distally from its distal end portion 18. The distal end tubes 50, 55, and 60 are capable of independent movement and are not attached to each other, but only to longitudinal member 12.

The first, second, and third passageways (52, 57, 62) in the distal end tubes have generally circular cross-sections. However, other shapes such as D-shape, oval, square, or triangular are also contemplated to be within the scope of the disclosure. Additionally, the cross-sections need not be identical. It is contemplated that passageways of different sizes and cross-sections may be used. It is further within the scope of the disclosure that the distal end tubes have varying diameters or distal end shapes. For example, the distal end tubes may have larger diameters proximate to elongated flexible tubular member 12 which transition to smaller diameter(s) proximate to the distal ends of the tubes. Lastly, it is preferable, but not necessary, that the tubes have blunt ends and that they are made of soft durometer material to avoid trauma to the vessel wall, which can lead to a vascular stenosis.

As shown in FIG. 1, the first distal end tube 50 has a length $L_b$ which is less than a length $L_c$ of the third distal end tube 60 when measured in a longitudinal direction along each of the distal end tubes 50 and 60 from the distal end 18 of elongated flexible tubular member 12 respectively to distal ends 53 and 63. And when similarly measured, the second distal end tube 55 has a length $L_a$ which is less than both $L_b$ of the first distal end tube 50 and $L_c$ of the third distal end tube 60. Positioning the aspiration ports (54 and 59) proximal to the infusion port 64 assures that a majority of the blood that is aspirated to the dialyzer (or other device) is not the same blood that has been previously cleansed and returned to the vessel through the infusion port 64.

FIG. 3 illustrates an alternative placement of three distal tubes to the distal end portion 18 of elongated flexible tubular member 12. The first distal end tube 70 has an outer surface 71 and defines a first passageway 72 extending longitudinally through distal end tube 70, terminating at aspiration port 74 at distal end 73. The second distal end tube 75 has an outer surface 76 and defines a second passageway 77 extending longitudinally through distal end tube 75, terminating at aspiration port 79 at distal end 78. The third distal end tube 80 has an outer surface 81 and defines a third passageway 82 extending longitudinally through distal end tube 80, terminating at infusion port 84 at distal end 83. The first and second passageways 72, 77 are in fluid communication with aspiration lumen 24, which extends the full length of catheter 10. Third passageway 82 is in fluid communication with infusion lumen 22, which also extends the full length of catheter 10.

The relationship of $L_d$, $L_e$, and $L_f$ depicted in FIG. 3 is slightly different from the embodiment depicted in FIG. 1. The first distal end tube 70 has a length $L_d$ which is less than a length $L_f$ of the third distal end tube 80 when measured in a longitudinal direction along each of the distal end tubes 70 and 80 from the distal end 18 of elongated flexible tubular member 12 respectively to distal ends 73 and 83. When similarly measured, the second distal end tube 75 has a length $L_e$ which is less than $L_f$ of the third distal end tube 80 but greater than $L_d$ of the first distal end tube 70.

Catheter 10 may be inserted into a blood vessel over a guide wire, for example, using the now well-known Seldinger percutaneous entry technique. Referring to FIG. 4, catheter 10 is, however, preferably first preloaded onto obturator 88. Obturator 88 is generally a hollow cannula, typically made of a plastic such as polytetrafluoroethylene, with a standard Luer lock 89 at its proximal end. The distal end of obturator 88 is fed into Luer lock 42, through flexible extension tube 34, through aspiration lumen 24, out aspiration port 54, then into side hole 90 (see also FIG. 1) in distal end tube 60 and out infusion port 64. Luer lock 89 is thereafter engaged with Luer lock 42 to hold obturator 88 in position inside catheter 10.

With catheter 10 thusly preloaded onto obturator 88, an introducer needle is then inserted into the patient's jugular or subclavian vein as is well known in the art to practice the Seldinger percutaneous entry technique. A guide wire is inserted through the needle and into the vein. The needle is then removed and the tissue surrounding the guide wire dilated with an appropriate sized dilator. Catheter 10 is then back loaded over the guide wire by inserting the proximal end of the guide wire into the distal open end 91 of obturator 88 and out Luer lock 89. Thusly positioned, the physician then feeds catheter 10 and obturator 88 over the guide wire and into the desired positioned within the vena cava vein or other desired vessel. The guide wire and obturator 88 are thereafter removed, which allows the now unjoined distal end tubes 50, 55, and 60 to separate and move freely inside the vessel.

Figure 5:
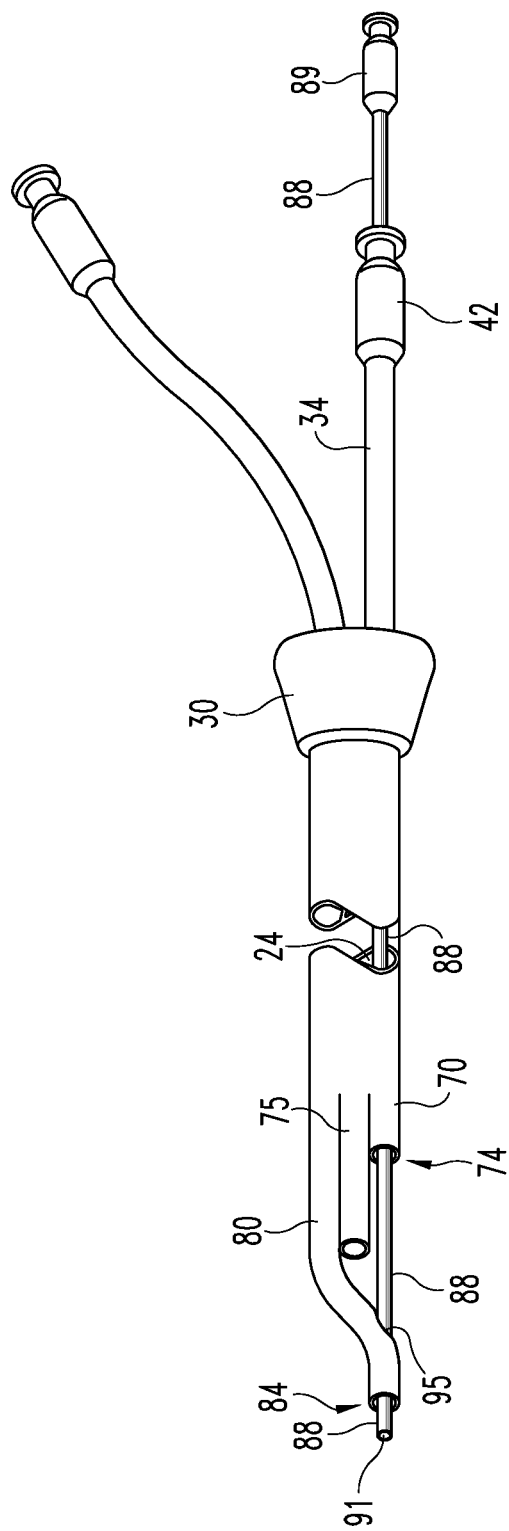
FIG. 5 depicts a plan view of another embodiment of the present disclosure preloaded onto an obturator.

The embodiment of the disclosure depicted in FIG. 3 can be similarly inserted within a blood vessel and is shown preloaded on obturator 88 in FIG. 5. The distal end of obturator 88 is fed into Luer lock 42, through flexible extension tube 34, through aspiration lumen 24, out aspiration port 74, then into side hole 95 (see also FIG. 3) in distal end tube 80 and out infusion port 84. Luer lock 89 is thereafter engaged with Luer lock 42 to hold obturator 88 in position inside catheter 10. Once catheter 10 and obturator 88 are similarly positioned within the a vessel (e.g. the vena cava vein) as previously described, the guide wire and obturator 88 are removed, which allows the now unjoined distal end tubes 70, 75, and 80 to separate and move freely inside the vessel.

The first, second, and third distal end tubes; the elongated flexible tubular body; the flexible extension tubes, and the hub, are all preferably made of biocompatible plastics or elastomers. Examples of suitable biocompatible plastics may be selected from materials such as polyurethane, polyethylene, vinyl acetates, and polyvinyl chloride. Examples of suitable biocompatible elastomers include medical grade silicone rubbers, polyvinyl chloride elastomers, polyolefin elastomers, and urethane-based elastomers. Should multilumen catheter 10 be used for hemodialysis, the first, second, and third distal end tubes and the elongated flexible tubular body are further preferably formed of a soft silicone elastomer which has a hardness of from about 75-A to about 85-A on a Shore durometer scale.

Figure 6:
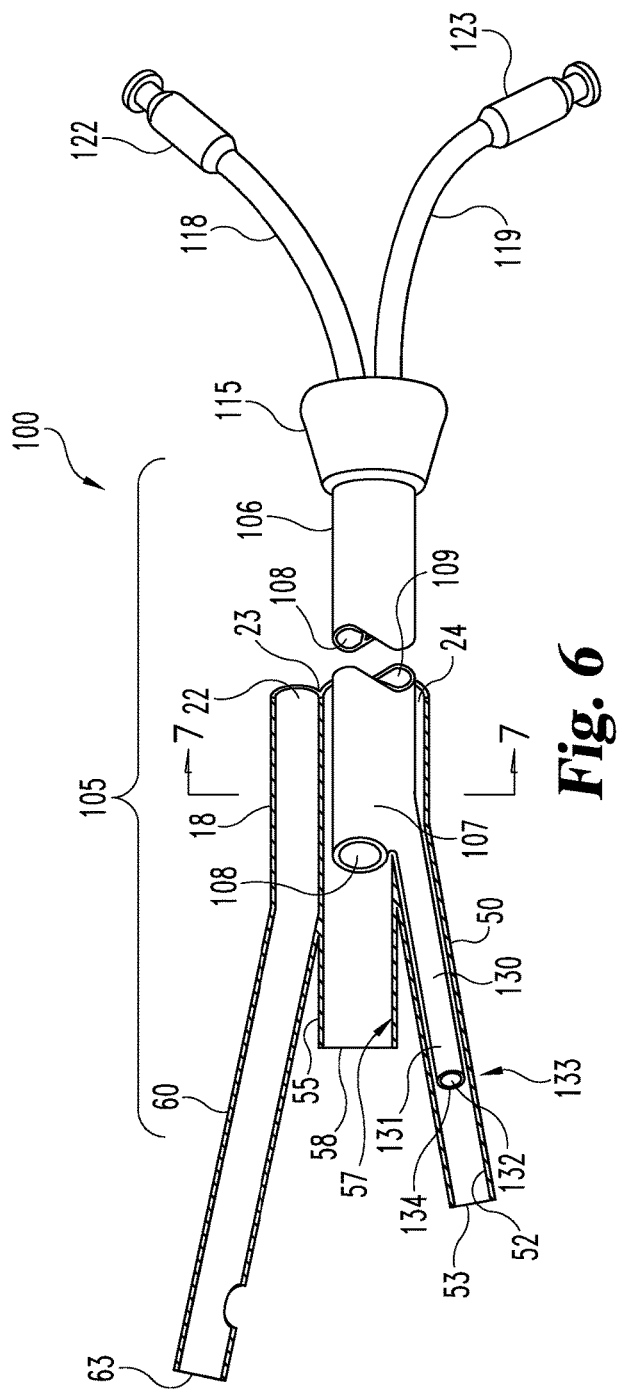
FIG. 6 depicts a plan view of yet another embodiment of the present disclosure that tests for occlusions.
Figure 7:
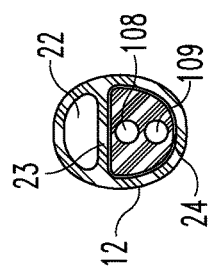
FIG. 7 depicts a sectional view of an embodiment of the present disclosure that tests for occlusions.

Referring now to FIG. 6, an occlusion testing device for an aspiration or infusion lumen with at least two distal end tubes is shown. FIG. 6 depicts testing device 100 according to one embodiment of the present disclosure. Occlusion testing device 100 is not shown to scale to avoid obscuring finer details. Testing device 100 includes an elongated tubular member 105 having a proximal end portion 106 and a distal end portion 107. Testing device 100 is shown in FIGS. 6 and 7 with two lumens extending through it, outflow lumen 108 and outflow lumen 109. Both are for aspiration. As shown, elongated tubular member 105 has a generally D-shaped cross-section to complement the previously described generally D-shaped open profile of aspiration lumen 24. Additional cross-sections are usable with this disclosure, such as round, oval, egg-shaped, or rectangular as needed to similarly complement the profiles of other aspiration or infusion lumens. Outflow lumens 108 and 109 preferably have round open profiles.

In the illustrated embodiment, testing device 105 includes a conventional bifurcated fitting at its proximal end, such as hub 115. Flexible extension tubes 118, 119 extend in the proximal direction from hub 115. Flexible extension tube 118 is in fluid communication with outflow lumen 108, and flexible extension tube 119 is in fluid communication with outflow lumen 109. Luer locks or other suitable connecting mechanisms 122, 123 are placed at the proximal ends of tubes 118, 119. Luer lock 122 provides fluid engagement with outflow lumen 108 and Luer lock 123 provides fluid engagement with outflow lumen 109.

Testing device 105 further includes at least one distal end tube 130 attached to and extending from or contiguous with the distal end portion 107. The distal end tube 130 has an outer surface 131 and defines passageway 132 extending longitudinally through distal end tube 130, and terminates with aspiration port 134 at distal end 133. The passageway 132 is in fluid communication with outflow lumen 109, which extends the full length of testing device 100.

The distal end tube 130 preferably has an outer surface that is continuous with the outer surface of elongated tubular member 105 and extends distally from the distal portion 107 of elongated tubular member 105. Distal end tube 130 has a generally round cross-section to complement the generally round-shaped open profile of passageway 52. Additional cross-sections are, however, usable with this disclosure, such as D-shaped, oval, egg-shaped, or rectangular to similarly complement other passageway profiles.

In an alternative embodiment, not shown, distal end tube 130 could be in fluid communication with outflow lumen 108 and have a cross-section to complement the open profile of passageway 57 of second distal end tube 55.

Occlusion testing device 100 is used by inserting its distal end first into aspiration lumen 24 of catheter 10. The distal end 133 of distal end tube 130 is fed into Luer lock 42 and through flexible extension tube 34 (see FIG. 4), through aspiration lumen 24, and then fed into passageway 52 of first distal end tube 50. (In an alternative embodiment, tube 130 can be fed into passageway 57 of second distal end tube 57). Thusly positioned inside catheter 10 as shown in FIG. 6, outflow lumen 108 of testing device 100 is placed in fluid communication with passageway 57 of second distal end tube 55. Outflow lumen 109 of testing device 100 is placed in fluid communication with passageway 52 of first distal end tube 50, e.g. with lumen 109 extending along a part of distal end tube 50.

The physician can now determine which of the two distal end tubes (50 or 55) may be occluded by aspirating through each of the lumens 108, 109. This can be accomplished, for example, by aspirating with a syringe (not shown) attached to each of Luer locks 122, 123. Thereafter the physician may pull thrombus formation or other movable blockage that may be present from the occluded distal end tube and through the outflow lumens in testing device 100 by applying vacuum to the outflow lumen which is not aspirating properly (108 or 109) at the respective Luer lock (122 or 123) for that lumen.

It will be understood that testing device 100 can be similarly used for an infusion lumen with two distal end tubes by inserting catheter 100 into the infusion lumen, instead of the aspiration lumen. In that way, any blockage that may be suspected in an infusion lumen(s) can be checked and alleviated.

Testing device 100 is preferably made of a sturdy material that will enable the user to perform the tests and tasks noted above. Particular materials for device 100 can include biocompatible metals, preferably with some flexibility to enable movement of device 100 within the catheter lumens to be tested. Polyurethane is another material that can be used for device 100, especially insofar as it may be less likely to damage the inside of the catheter lumen through which it is extended than metals. Other biocompatible materials could also be used.

While the disclosure has been illustrated and described in detail in the drawings and foregoing description, the same is to be considered as illustrative and not restrictive in character, it being understood that only embodiments have been shown and described and that all changes, equivalents, and modifications that come within the spirit of the disclosures defined by the following claims are desired to be protected. Particular features described with respect to one embodiment or structure are usable with other embodiments or structures disclosed herein.

What is claimed is:

1. A multilumen catheter assembly, comprising:
   an elongated flexible tubular member having a proximal end portion and a distal end portion with a distal tip, the elongated flexible tubular member also having at least one septum forming at least one aspiration lumen and at least one infusion lumen extending between the proximal end portion and the distal tip of the distal end portion;
   a first distal end tube attached to the distal tip of the distal end portion of the elongated flexible tubular member, the first distal end tube having open proximal and distal ends and in fluid communication with said aspiration lumen, the first distal end tube having a first longitudinal length between its proximal and distal ends;

a second distal end tube attached to the distal tip of the distal end portion of the elongated flexible tubular member, the second distal end tube having open proximal and distal ends and in fluid communication with said aspiration lumen or said infusion lumen, the second distal end tube having a second longitudinal length between its proximal and distal ends, the second distal end tube having a longitudinal axis;

a third distal end tube attached to the distal tip of the distal end portion of the elongated flexible tubular member, the third distal end tube having open proximal and distal ends and in fluid communication with said infusion lumen, the third distal end tube having a third longitudinal length between its proximal and distal ends, the third longitudinal length being greater than the second longitudinal length so that the third distal end tube includes a leading segment extending distally of the distal end of the second distal end tube;

wherein the distal ends of said first, second, and third distal end tubes are not attached to each other and the distal ends are thereby capable of independent movement;

wherein the second distal end tube is positioned laterally between the first distal end tube and third distal end tube;

wherein the third distal end tube has a side hole in the wall of the of the third distal end tube;

wherein the outer surfaces of the first, second and third distal end tubes are continuous with the outer surface of the elongated flexible tubular member; and wherein the first longitudinal length is greater than the second longitudinal length; and an obturator passing through the first distal end tube, out of the open distal end of the first distal end tube, into the side hole of the third distal end tube, and out of the open distal end of the third distal end tube, wherein the leading segment of the third distal end tube is held in said assembly in a curved path crossing over the longitudinal axis of the second distal end tube.

2. The multilumen catheter assembly of claim 1, where said at least one aspiration lumen has a D-shaped open profile.

3. The multilumen catheter assembly of claim 1, where said at least one infusion lumen has a D-shaped open profile.

4. The multilumen catheter assembly of claim 1, where said aspiration lumen has an open profile, said infusion lumen has an open profile, and the open profile of the aspiration lumen is larger than the open profile of the infusion lumen.

5. The multilumen catheter assembly of claim 1, where said second distal end tube is in fluid communication with said aspiration lumen.

6. The multilumen catheter assembly of claim 1, where said second distal end tube is in fluid communication with said infusion lumen.

7. The multilumen catheter assembly of claim 1, where the first, second, and third distal end tubes are substantially cylindrical.

8. The multilumen catheter assembly of claim 1, wherein the first, second and third distal end tubes are made of biocompatible elastomer.

9. The multilumen catheter assembly of claim 8, wherein the elastomer is a silicone elastomer, polyvinylchloride elastomer, polyolefin elastomer, or urethane elastomer.

10. The multilumen catheter assembly of claim 9, wherein the biocompatible elastomer is a silicone elastomer.

11. The multilumen catheter assembly of claim 10, wherein the silicone elastomer has a Shore hardness of about 75-A to about 85-A.

* * * * *